United States Patent [19]

Ryan

[11] Patent Number: 4,551,145
[45] Date of Patent: Nov. 5, 1985

[54] SANITARY NAPKIN

[76] Inventor: Lizabeth L. Ryan, Music Vale Rd., Salem, Conn. 06415

[21] Appl. No.: 609,591

[22] Filed: May 14, 1984

[51] Int. Cl.$^4$ .............................................. A61F 13/16
[52] U.S. Cl. ................................. 604/389; 604/385 R
[58] Field of Search ................ 604/389, 385, 393, 390

[56] References Cited
U.S. PATENT DOCUMENTS

| | | |
|---|---|---|
| 3,024,788 | 3/1962 | Lane . |
| 3,035,578 | 5/1962 | Elmore . |
| 3,230,956 | 1/1966 | Kargul . |
| 3,274,999 | 9/1966 | Robinson . |
| 3,604,423 | 9/1971 | Fraser . |
| 3,626,945 | 12/1971 | Mobley . |
| 3,672,371 | 6/1972 | Roeder . |
| 3,731,689 | 5/1973 | Schaar ................................ 604/385 |
| 3,920,019 | 11/1975 | Schaar ................................ 604/385 |
| 3,973,567 | 8/1976 | Srinivasan et al. . |
| 4,085,753 | 4/1978 | Yellert ................................ 604/385 |
| 4,182,336 | 1/1980 | Black . |
| 4,430,087 | 2/1984 | Azpiri ................................. 604/385 |

Primary Examiner—John D. Yasko
Assistant Examiner—Christa K. Scott
Attorney, Agent, or Firm—Prutzman, Kalb, Chilton & Alix

[57] ABSTRACT

A sanitary napkin is disclosed comprising an elongated wad of absorbent material, a sheet member of substantially moisture-impervious, flexible material of sufficient dimensional size to form an enclosure of the wad for disposal and being folded in a first configuration to form a flat, moisture shield covering the lower surface of the wad and being invertible into a second configuration to form an enclosure of the wad with the enclosure having a sealable opening, the sheet element being disposed adjoining the lower surface of the wad and having first and second opposing side portions facing away from the lower surface of the wad in the first configuration, the side portions defining a sealable opening when the sheet is inverted into the second configuration to form an enclosure for the wad, and pressure adhesive material disposed on the first and second side portions of the sheet member for attaching the wad to a supporting garment for wearing in the first configuration and for sealing closed the sealable opening of the enclosure when the sheet member is inverted into the second configuration for disposal.

25 Claims, 3 Drawing Figures

SANITARY NAPKIN

BACKGROUND AND SUMMARY OF THE INVENTION

The present invention generally relates to a sanitary napkin and more particularly to a sanitary napkin having a means for convenient and hygienic disposal after use.

After use, sanitary napkins and pads present somewhat unique disposal problems. First, sanitary napkins are generally too bulky for disposal through conventional sewage and septic systems and tend to cause clogging and blockage. Additionally, the presence of a nonbiodegradable moisture shield renders the napkin particularly unsuitable for disposal through a septic system.

Since soiled napkins are generally moist, unsightly in appearance and may exhibit an unpleasant odor, they are unsuited for bare disposal in a waste paper basket or the like. Furthermore, there is an understandable reluctance toward any extensive handling of a soiled napkin. As a result, despite the significant damage inflicted on plumbing systems, people continue to attempt to flush napkins through sewage and septic systems because of the unavailability of a suitable means for disposal.

Heretofore, many attempts have been made to provide a suitable means for disposing of sanitary napkins such as the devices shown in the following patents: Lane U.S. Pat. No. 3,024,788 issued Mar. 13, 1962; Elmore, U.S. Pat. No. 3,035,578 issued May 22, 1962, Kargul, U.S. Pat. No. 3,230,956 issued Jan. 25, 1966; Robinson, U.S. Pat. No. 3,274,999 issued Sept. 27, 1966; Fraser, U.S. Pat. No. 3,604,423 issued Sept. 14, 1971; Mobley, U.S. Pat. No. 3,626,945 issued Dec. 14, 1971; Srinivasan et al, U.S. Pat. No. 3,973,567 issued Aug. 10, 1976; and Black, U.S. Pat. No. 4,182,336 issued Jan. 8, 1980. These attempts at solving the problem of disposal have apparently been unsuccessful since there appears to be no sanitary napkin commerically available having a self-contained means for disposal despite the plethora of attempts to accomplish this end.

Importantly, it is desirable that a sanitary napkin having a self-contained means for disposal be cost efficient to manufacture.

Accordingly, it is an object of the present invention to provide a sanitary napkin with a self-contained enclosure for disposal which is economical to manufacture.

Another object of the invention is to provide a sanitary napkin having an easily manipulated, self-contained sealable disposal bag which is formed out of preexisting napkin components.

A further object of the invention is to provide a sanitary napkin having a moisture shield which is invertible after use to form an enclosure for disposal.

Another object of the invention is to provide a sanitary napkin having a self-contained enclosure for disposal with adhesive strips which perform a dual function of securing the napkin to an undergarment during use and sealing closed the enclosure for disposal after use.

A still further object of the invention is to provide a sanitary napkin with a self-contained enclosure for disposal which is easily and conveniently manipulated and inverted to form the enclosure without undue contact with the soiled napkin.

Yet another object of the invention is to provide a sanitary napkin having a self-contained enclosure for disposal which effectively does not increase the bulkiness of the napkin.

Still another object of the invention is to provide a sanitary napkin with a self-contained enclosure for disposal which effectively seals the soiled napkin within the enclosure to contain odors and moisture.

Yet another object of the invention is to provide a new and improved method of manufacturing a sanitary napkin having a self-contained enclosure bag for disposal.

It has been found that the foregoing and related objects and advantages may be obtained in a sanitary napkin comprising an elongated wad of absorbent material having an upper surface and a lower surface adapted to face away from the wearer's body. A sheet member of substantially moisture-impervious flexible material of sufficient dimensional size to form an enclosure of the wad is folded into a first configuration to form a moisture shield covering the lower surface of the wad and which is invertible into a second configuration to form an enclosure of the wad with a sealable opening. The sheet member is disposed adjoining the lower surface of the wad and has first and second opposite side portions facing away from the lower surface of the wad in the first configuration. The side portions define the sealable opening when the sheet is inverted in the second configuration to form the enclosure for the wad. Pressure adhesive means are disposed on at least one of the first and second side portions of the sheet member for attaching the wad to a supporting garment for wearing in the first configuration and for sealing closed the sealable opening of the enclosure when the sheet member is inverted into the second configuration for disposal. Alternately, strips of pressure adhesive material may be disposed on the first side portion and on the second side portion so that the adhesive strips engage each other for enhanced sealing of the sealable opening when the sheet element is inverted into the second configuration.

In an alternate embodiment, the sanitary napkin includes an elongated wad of absorbent material having an upper surface and a lower surface with the lower surface adapted to face away from a wearer's body. A fabric-like cover is disposed about the wad. An invertible bag member of substantially moisture-impervious flexible material and sufficient size to enclose the wad is disposed between the wad and the cover adjacent the lower surface of the wad. The bag member is folded into a first configuration to form a moisture shield covering the lower surface of the wad so as to be invertible inside-out into a second configuration enclosing the wad. Pressure adhesive means for attaching the wad to a supporting garment is disposed on the napkin.

A method of manufacturing a sanitary napkin of the type having a moisture shield sheet covering the bottom surface of the wad of absorbent material is also disclosed wherein the improvement comprises providing a sheet member of sufficient dimensional size to form an enclosure of the wad. The opposing sides of the sheet are fan-folded to form a flat moisture shield covering the lower surface of the wad which is invertible to form an enclosure for the wad. The sheet member is connected to the lower surface of the wad and pressure adhesive material is applied upon the fan-folded opposing sides of the sheet which face away from the lower surface of the wad to provide an adhesive means for attaching the wad to an undergarment for wearing and for sealing the enclosure of the wad after the sheet member is inverted. The pressure adhesive material is covered with a removable protective sheet.

DESCRIPTION OF THE PREFERRED EMBODIMENT

Figure 1:
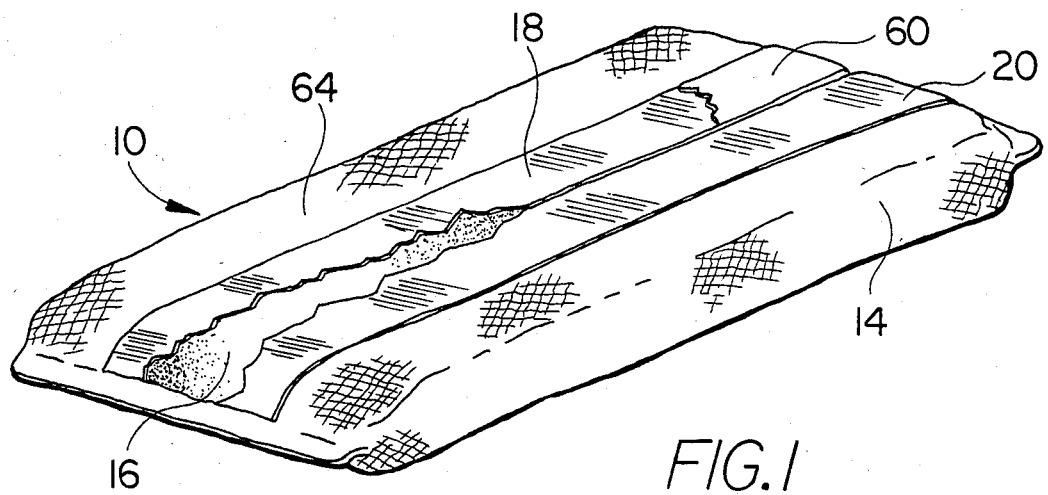
FIG. 1 is a diagrammatical perspective view of the lower surface of the napkin of the present invention partially broken away to show a portion of the folded sheet member.
Figure 2:
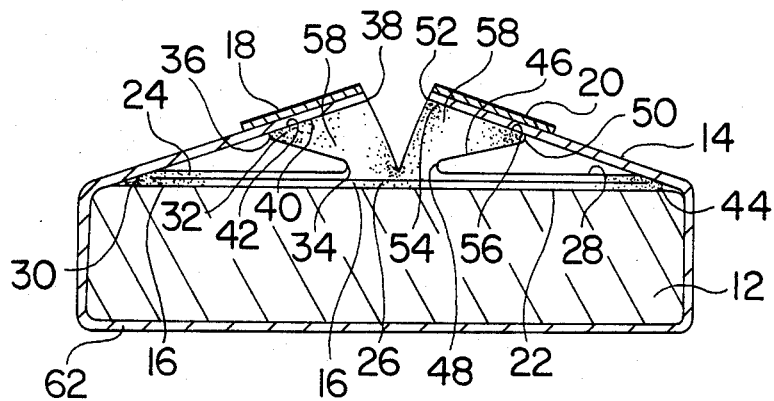
FIG. 2 is an enlarged cross-sectional view of the napkin of the present invention with the sheet member shown in an initial position of being inverted.

Referring to FIGS. 1 and 2 of the drawing, the sanitary napkin of the present invention is generally designated by the numeral 10 and comprises an elongated wad of absorbent material 12, a cover 14, a sheet member 16, and two elongated strips 18, 20 of pressure adhesive material.

The sheet member 16 is comprised of a substantially moisture-impervious flexible opaque material such as polyvinyl and is of sufficient dimensional size to form an enclosure for the wad 12. As will be described, the sheet member 16 is folded into a flat first configuration which is invertible inside-out into a second configuration which forms an enclosure having an opening which is tightly sealable by the adhesive strips 18, 20.

Specifically, the sheet member 16 comprises a first side fold portion 24, a middle portion 26, and an opposing side fold portion 28. In the illustrated embodiment of FIG. 2, the side fold portion 26 is folded about the fold line 30 (which is shown going into the plane of FIG. 2) back upon the middle portion 26 toward the centerline of the sheet member. The inner end portion 32 of the side fold portion 24 is fan-folded about fold line 34 and fold line 36 so that the longitudinal edge 38 of the side fold portion 24 extends generally along the centerline of the middle portion 26. The side segment 40 of the inner end portion 32 between the fold line 36 and the longitudinal edge 38 has a outer surface 42 which faces outwardly from the lower surface 22 of the wad when the sheet member is in the first configuration.

Similarly, the opposing side fold portion 28 is folded about a fold line 44 back against the middle portion 26 toward the centerline thereof. The inner end portion 46 of the side fold portion 28 is fan-folded about the fold line 48 and the fold line 50 so that the longitudinal edge 52 extends generally along the centerline of the middle portion 26. The side segment 54 of the inner end portion 46 also has an outer surface 56 which faces outwardly from the lower surface 22 of the wad when the sheet member is in the first configuration.

The opposite ends 58 (only one of which is shown) of the sheet member 16 are sealed to form sealed ends when the sheet member is in first configuration. Thus, a flat, invertible enclosure or bag member is formed which may be simply inverted inside-out to form a bag or pouch as shown in FIG. 3 with an opening being defined by the longitudinal edges 38, 52.

Figure 3:
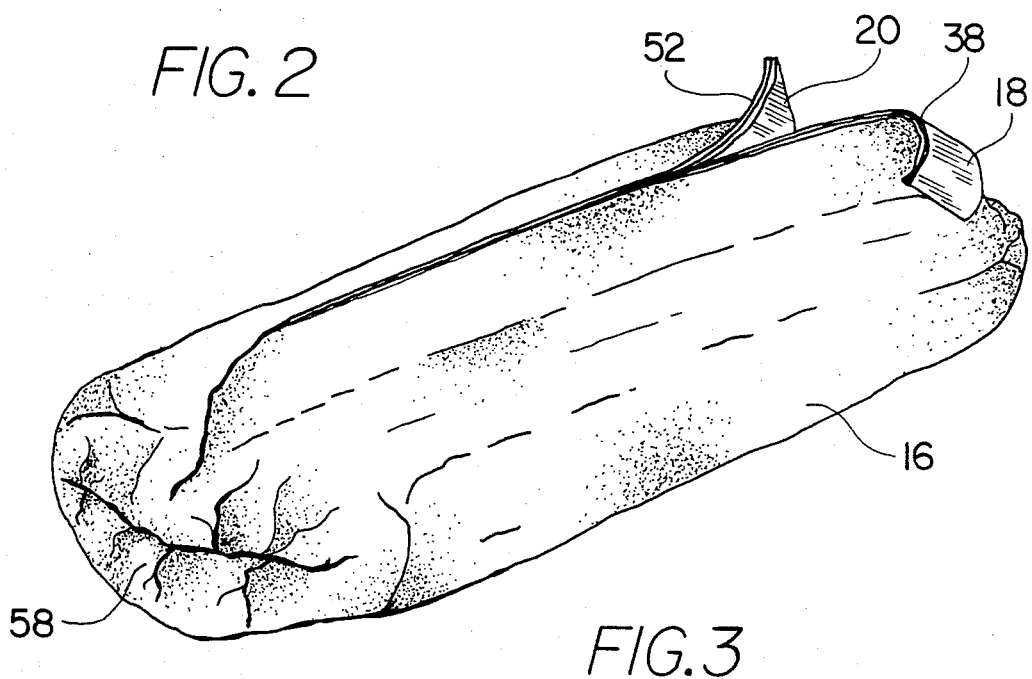
FIG. 3 is a diagrammatical perspective view of the sheet member inverted to form an enclosure of the wad with the enclosure opening being partially sealed closed.

Referring to FIG. 2, it is understood that FIG. 2 depicts the sheet member 16 in an interim position between the flat first configuration and the inverted enclosure configuration of FIG. 3. However, in the first configuration, the sheet member 16 is substantially flat so as not to increase the bulkiness of the napkin and is disposed against the lower surface 22 of the napkin to form a moisture shield. The moisture shield operates to retain menstrual flow thereby preventing leakage and the staining of clothes. The sheet member 16 in the first configuration covers the lower surface 22 of the wad and may extend up the sides of the wad so as to form a dish for retaining liquid.

The adhesive strips 18, 20 are comprised of pressure adhesive material such as the type disclosed in Roeder, U.S. Pat. No. 3,672,371, issued June 27, 1972. The strips 18, 20 extend longitudinally overlaying the side segments 40, 54 of the sheet member 16 so as to provide adhesive means for securing the napkin to an undergarment during use.

In the illustrated embodiment, the cover 14 is comprised of a soft, fabric-like material which covers the wad 12 and sheet member 16 extending to the longitudinal edges 38, 52 with the adhesive strips 18, 20 overlaying a portion of the cover 14. The cover 14 is utilized to prevent the sheet member 16 from irritating the skin of the legs of the wearer and so is preferably soft and nonirritating to the skin. The cover 14 also encloses the wad 12 and is therefore liquid pervious.

The pressure adhesive material of the adhesive strips 18, 20 may be of the type which will penetrate the material of cover 14 so that the adhesive adheres the cover to the side segments 40, 54 of the sheet member 16 for stability of the napkin assembly. Additionally, the cover 14 may extend beyond the opposite ends of the wad 12 and the adhesive strips 18, 20 may also extend past the ends of the wad to thereby seal the cover 14 at each end of the wad for further stability. In this manner, the adhesive strips 18, 20 perform a triple function in the napkin assembly, i.e., for attachment of the napkin to an undergarment during use, for sealing the enclosure for disposal after use, and for attaching the cover to the sheet element and sealing the cover ends.

Alternately, the cover 14 may extend up to the inner end portions 32, 46 of the side fold portions 24, 28 or a soft material may be adhered directly to the outwardly facing surface of the sheet member 16. Although less acceptable, the cover over the sheet member 16 may be dispensed with although discomfort could occur during use.

In use, the protective layer of paper 60 over adhesive strips 18, 20 is removed and the napkin is positioned such that the lower surface of the wad 22 faces away from the wearer's body and the adhesive strips 18, 20 secure the napkin to an undergarment. After use, the upper portion 62 of the napkin 10 is somewhat soiled and handling thereof is reduced to a minimum by holding the opposite sides of the lower surface 64 of the napkin and inverting the sheet member 16 inside-out to enclose the soiled wad 12 within the sheet member 16.

FIG. 2 depicts the sheet member 16 at the initial stage of inversion and FIG. 3 depicts the sheet member at the final stage of sealing the opening of the enclosure. Upon inversion, the sealed ends 52 of the sheet member 16 are pleated or puckered inwardly and the adhesive strip 18 engages the adhesive strip 20 to seal and close the opening of the bag to thereby retain odor and liquid. It is preferred that at least two strips of adhesive material be utilized to ensure adequate attachment and stability of the napkin to the undergarment and to ensure an effective seal of the opening of the bag. However, alternate configurations may be utilized such as a single strip of adhesive on one of the side segments 40, 54. Additionally, other configurations of adhesive material rather than longitudinal strips may also be acceptable. Furthermore, alternate configurations of the dual-function sheet member 16 may be utilized. Although less desirable, the sealed ends 58 may be omitted so that there is partial exposure of the soiled wad when the sheet member is inverted into the second configuration.

An improved method for manufacturing a sanitary napkin according to the present invention is provided which configures a sheet element for performance of a dual-function (i.e., moisture shield and disposal bag) and configures pressure adhesive strips for performance of a dual-function (or triple-function) (i.e., attachment to the undergarment, sealing the bag opening, and stability of the napkin assembly). As can be appreciated from the foregoing description, the method of manufacturing includes providing a sheet member of moisture-impervious material of sufficient dimensional size to form an enclosure of the wad. The opposing sides of the sheet member are fan-folded so as to form a flat moisture shield for covering the lower surface of the wad and which is invertible to form an enclosure for the wad. Pressure adhesive material is applied upon the fan-folded opposing sides of the sheet member which face away from the wad so as to provide an adhesive means for attaching the napkin to a supporting garment for wearing and for sealing the enclosure after inversion of the sheet member. The sheet member is connected to the lower surface of the wad through either an enclosing cover of fabric-like material or by other adhesive means. The pressure adhesive material is covered by a protective sheet of paper which is removable prior to use. Alternately, the pressure adhesive material may be applied so as to secure the fabric-like cover to the sheet element.

Thus it can be seen that the sanitary napkin of the present invention is economical to manufacture and provides an easily manipulated, self-contained sealable disposal bag formed of preexisting napkin components. Convenient and hygienic disposal is obtained with a self-contained enclosure which seals in odors and moisture yet does not add bulkiness to the napkin.

As will be apparent to persons skilled in the art, various modifications and adaptations of the structure above described will become readily apparent without departure from the spirit and scope of the invention, the scope of which is defined in the appended claims.

I claim:

1. A sanitary napkin comprising,
   an elongated wad of absorbent material having an upper surface and a lower surface with said lower surface adapted to face away from a wearer's body,
   a sheet member of substantially moisture-impervious flexible material of sufficient dimensional size to form an enclosure of said wad for disposal and being folded in a first configuration to form a moisture shield covering the lower surface of said wad and being invertible into a second configuration to form an enclosure for said wad with said enclosure having a sealable opening,
   said sheet member being disposed adjoining said lower surface of said wad and having first and second opposing side portions facing away from said lower surface of said wad in said first configuration, said side portions defining said sealable opening when said sheet is inverted into said second configuration to form an enclosure for said wad, and
   pressure adhesive means disposed on at least one of said first and second side portions of the sheet member for attaching said wad to a supporting garment for wearing in said first configuration and for sealing closed said sealable opening of said enclosure when said sheet member is inverted into said second configuration for disposal.

2. The device of claim 1 wherein said pressure adhesive means comprises a strip of pressure adhesive material.

3. The device of claim 2 wherein said strip of pressure adhesive material on one of said first and second side portions sealingly engages the other of said first and second side portions to seal said opening of said enclosure upon inversion of said sheet member to form said enclosure.

4. The device of claim 1 wherein said pressure adhesive means comprises a first strip of pressure adhesive material disposed on said first side portion and a second strip of pressure adhesive material disposed on said second side portion so that said first strip sealingly engages said second strip to seal said opening of said enclosure upon inversion of said sheet member to form said enclosure.

5. The device of claim 4 wherein said first and second side portions each have an inner edge and said pressure adhesive strips are disposed adjacent said respective inner edges.

6. The device of claim 1 wherein,
   said first side portion of said sheet member is folded back upon said sheet member toward the centerline of said sheet member with an outer surface facing away from said lower surface of said wad when said sheet member is in said first configuration,
   said second side portion of said sheet member is folded back upon said sheet member toward the centerline of said sheet member with an outer surface facing away from said lower surface of said wad when said sheet member is in said first configuration, and
   said pressure adhesive means being disposed on one of said outer surface of said first side portion and said outer surface of said second side portion with said outer surface of said first side portion adapted to adjoin the outer surface of said second side portion when said sheet member is inverted into said second configuration.

7. The device of claim 6 wherein,
   said first side portion has an inner edge extending longitudinally along said sheet member, and
   said second side portion has an inner edge extending longitudinally along said sheet member generally parallel to said inner edge of said first side portion.

8. The device of claim 7 wherein said inner edges of said first and second side portions extend generally along the centerline of said sheet member in adjacent disposition.

9. The device of claim 8 wherein said pressure adhesive means comprises a first strip of pressure adhesive material extending along the inner edge of said first side portion and a second strip of pressure adhesive material extending along the inner edge of said second side portion.

10. The device of claim 6 wherein said first and second side portions are each fan-folded.

11. The device of claim 10 wherein said sheet member has opposing sealed ends.

12. The device of claim 10 which comprises a fabric-like cover about said wad and said sheet member in said first configuration.

13. The device of claim 1 wherein said sheet member has opposing sealed ends.

14. The device of claim 1 which comprises a fabric cover about said wad and said sheet member in said first configuration.

15. The device of claim 14 wherein said fabric cover is interposed between said pressure adhesive means and said sheet member.

16. The device of claim 15 wherein said pressure adhesive means also adheres said cover to said first and second side portions of said sheet member.

17. The device of claim 1 wherein said sheet member is opaque so that said wad is not visible through said sheet member when said sheet member is inverted into said second configuration to enclose said wad.

18. A sanitary napkin comprising,
  an elongated wad of absorbent material having an upper surface and a lower surface with said lower surface adapted to face away from a wearer's body,
  a fabric-like cover disposed about said wad,
  an invertible bag member of substantially moisture-impervious flexible material and sufficient size to enclose said wad,
  said bag member being disposed between said wad and said cover adjacent said lower surface of said wad and being folded into a first configuration to form a moisture shield covering the lower surface of said wad and so as to be invertible inside-out into a second configuration enclosing said wad, and
  pressure adhesive means for attaching said wad to a supporting garment.

19. The device of claim 18 wherein said bag member has opposing first and second side portions defining an opening in said bag member when said bag member is in said first configuration, said cover extending to said opening.

20. The device of claim 19 wherein said pressure adhesive means comprises,
  a first adhesive strip on said cover overlaying said first side portion and extending adjacent said opening, and
  a second adhesive strip on said cover overlaying said second side portion and extending adjacent said opening, said first and second adhesive strips being adapted for attaching said wad to a supporting garment for wearing in said first configuration and for sealing closed said opening of said bag member when said bag member is inverted inside-out into said second configuration enclosing said wad and cover for disposal.

21. The device of claim 20 wherein said first adhesive strip adheres said cover to said first side portion and said second adhesive strip adheres said cover to said second side portion.

22. The device of claim 18 wherein said bag member is opaque so that said wad is not visible through said bag member when said bag member is inverted into said second configuration to enclose said wad.

23. A method of manufacturing a sanitary napkin of the type having a moisture shield sheet covering the bottom surface of the wad of absorbent material wherein the improvement comprises,
  providing a sheet member of sufficient dimensional size to form an enclosure of the wad,
  fan-folding the opposing sides of the sheet to form a flat moisture shield for covering the lower surface of the wad which is invertible to form an enclosure for the wad,
  connecting the sheet member to the lower surface of the wad,
  applying pressure adhesive material upon the fan-folded opposing sides of the sheet which face away from the wad to provide an adhesive means for attaching the napkin to a supporting garment for wearing and for sealing the enclosure for the wad after the sheet member is inverted, and
  covering the pressure adhesive material with a removable protective sheet.

24. The method of claim 23 which comprises enclosing the wad and sheet member in a fabric-like cover.

25. The method of claim 24 which comprises applying the pressure adhesive material upon the portion of the cover overlaying the fan-folded opposing sides of the sheet to adhere the cover to the sheet.

* * * * *